United States Patent
Su et al.

(10) Patent No.: US 6,313,134 B1
(45) Date of Patent: Nov. 6, 2001

(54) USES OF THALIPORPHINE OR ITS DERIVATIVES IN TREATMENT OF CARDIAC DISEASES AND PREPARATION OF SAME

(75) Inventors: Ming-Jai Su; Shoei-Sheng Lee, both of Taipei (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/644,932

(22) Filed: Aug. 23, 2000

(30) Foreign Application Priority Data

May 4, 2000 (TW) .............................. 089108508

(51) Int. Cl.$^7$ .......................... A61K 31/473; A61P 9/06; C07D 221/18
(52) U.S. Cl. .............................................. 514/284; 546/75
(58) Field of Search .............................. 546/75; 514/284

(56) References Cited

U.S. PATENT DOCUMENTS 4,202,980 * 5/1980 Hartenstein .............................. 546/75
4,309,542 * 1/1982 Hartenstein .............................. 546/75
4,461,895 * 7/1984 Fritschi .................................. 546/75

OTHER PUBLICATIONS

Bundgaard H. Design of Prodrugs. Elsevier. Amsterdam–New York–Oxford. pp. 1–3, 1985.*
Su MJ et al. Eur. J. Pharmacol. 254(1–2), 141–50, 1994.*

* cited by examiner

Primary Examiner—Evelyn Mei Huang
(74) Attorney, Agent, or Firm—Christensen O'Connor; Johnson Kindness PLLC

(57) ABSTRACT

The present invention discloses thaliporphine and its derivatives for the treatment and/or prophylaxis of cardiac diseases, including cardiac arrhythmia, myocardial ischemia or myocardial infarction, and sudden death caused by cardiac arrhythmia or acute myocardial infarction.

5 Claims, 9 Drawing Sheets

USES OF THALIPORPHINE OR ITS DERIVATIVES IN TREATMENT OF CARDIAC DISEASES AND PREPARATION OF SAME

BACKGROUND OF THE INVENTION

1. Field of the Invention

The present invention relates to pharmaceutical compositions useful for the treatment and/or prophylaxis of cardiac diseases. More particularly, it relates to the use of thaliporphine or its derivatives as the active ingredient for the treatment and/or prophylaxis of cardiac diseases.

2. Description of the Related Arts

Recently, the worldwide aged population has been increasing. This is primarily due to improvements in medicine and life-style. However, aging usually is accompanied by an increase of cardiovascular related diseases. Examples include angina pectoris, acute myocardial infarction and coronary artery atherosclerosis, which are associated with the systole and embolism of the vessels. In addition, the embolism of the coronary artery usually results in cardiac hypertrophy, inducing heart failure and arrhythmia. Similarly, cardiac arrhythmia is frequently associated with myocardial ischemia. Malignant ventricular arrhythmias causing collapse is generally believed to be the major mechanism responsible for sudden death. Reperfusion following the release of occluded coronary artery is also associated with arrhythmia. Such arrhythmia may increase the mortality and morbidity of thrombolytic therapy and coronary angioplasty. Several causes for this reperfusion arrhythmia have been proposed. Among them, the generation of oxygen free radicals and their subsequent peroxidation of membrane lipids is perceived as a major cause of reperfusion arrhythmia.

The drugs used for treating patients with heart failure include diuretic, digitalis, vasopressin transferase inhibitor, sympathetic nerve activator or phosphodiesterase inhibitor. Among them, digitalis, sympathetic nerve activator or phosphodiesterase inhibitor can markedly enhance the systole; these drugs however may induce cardiac arrhythmia or tachyrhythmia. Thus, there is no ameliorated effect on the survival of patients by administering those drugs over a long period of time. Recently, an ameliorated effect on the survival of patients with heart failure has been confirmed by administering vasopressin receptor blocker, vasoendotheliosin receptor blocker, and Carvedilol with the blocking activities of sympathetic α- and β-adrenoceptors, respectively (Ye T L, et al., *J. Pharmacol. Exp. Ther.*, 1992, 263:92–98; Bristow M R, et al., *Circulation*, 1996, 94:2807–2816; Colucci W S, et al., *Circulation*, 1996, 94:2800–2806).

Because of the close relationship among occluded coronary artery, heart failure and cardiac arrhythmia, a traditional drug, ouabain, when used as a treatment for heart failure, can enhance the systole, but usually induces cardiac arrhythmia. Thus, the drug is not beneficial to increasing the survival rate of the patients. Therefore, there is still a need to search for the effective agent to suppress arrhythmia, cardiac infarction and the progression of heart failure resulting from an acute coronary attack.

Some compounds have been reported to have the ability to enhance the systole, such as synthetic 2-phenyl-4-oxohydroquinoline (Su M J, et al., *Brit. J. Pharmacol.*, 1993, 110:310–316), thaliporphine of Lauraceae and Rutaceae (Su M J, et al,. *Eur. J. Pharmacol.*, 1994, 254:141–150), liriodenine of *Fissistigma glaucescens* (Chang G J, et al., *Brit. J. Pharmacol.*, 1996, 118:503–512), (−)-caryachine of *Cryptocarya chinensis* (Wu M H, et al., *Brit. J. Pharmacol.*, 1995, 116:3211–3218) and berberine derivatives; wherein the liriodenine, (−)-caryachine and berberine derivatives have been confirmed to exhibit antiarrhythmic ability. Conventionally, the effect of antiarrhythmic ability is evaluated by induced arrhythmia using an isolated rat heart subjected to 30 minutes ligation followed by reperfusion. However, the $K^+$ outward current found in other animals is slightly different from a rat. Therefore, in these trials, guinea pigs were also used as subjects to exhibit this difference in $K^+$ outward current. In addition, Su et al. (1994, supra) shows that the thaliporphine possesses the ability to enhance systole and $Ca^{2+}$ inward currents. Because the enhancement of systole is not beneficial for ischemic myocardial necrosis, drugs with these functions are theoretically useless for treating myocardial infarction and arrhythmia. However, the present invention indeed demonstrates that thaliporphine and its derivatives, particularly in small dosages, are useful for the treatment and/or prophylaxis of cardiac diseases.

SUMMARY OF THE INVENTION

One aspect of the present invention features a pharmaceutical composition for the treatment and/or prophylaxis of a cardiac disease in a mammal, comprising an effective amount of a compound of formula I:

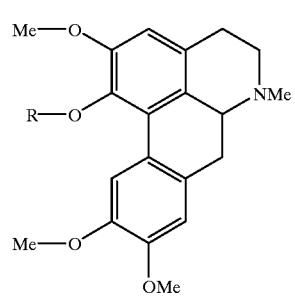

or ester derivatives thereof, wherein R is hydrogen, acetyl, propionyl, butyryl or tert-butoxycarbonyl, or their pharmaceutically acceptable salts; and a pharmaceutically acceptable carrier or excipient.

Another aspect of the present invention features a compound of formula I:

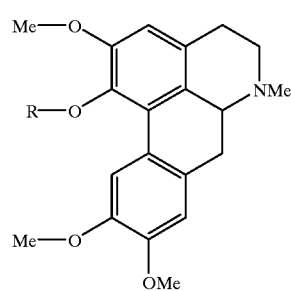

wherein R is propionyl, butyryl or tert-butoxycarbonyl, or their pharmaceutically acceptable salts.

Another aspect of the present invention features a compound of formula II and a pharmaceutical composition comprising the same active ingredient as for the treatment and/or prophylaxis of a cardiac disease in a mammal. The pharmaceutical composition comprises an effective amount of a compound of formula II:

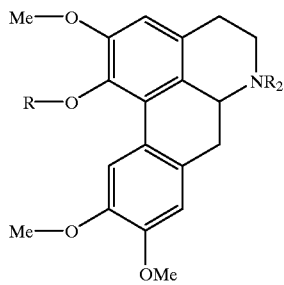

II or ester derivatives thereof, wherein $R_1$ is hydrogen, acetyl, propionyl, butyryl or tert-butoxycarbonyl; and $R_2$ is ethyl, allyl, propyl, butyl, isobutyl or cyclopropylmethyl, or their pharmaceutically acceptable salts; and a pharmaceutically acceptable carrier or excipient.

Yet another aspect of the present invention features a compound of formula III and a pharmaceutical composition comprising the same active ingredient as for the treatment and/or prophylaxis of a cardiac disease in a mammal. The pharmaceutical composition comprises an effective amount of a compound of formula III:

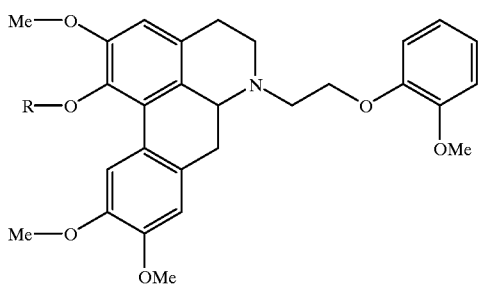

III or ester derivatives thereof, wherein R is hydrogen, acetyl, propionyl, butyryl or tert-butoxycarbonyl; or their pharmaceutically acceptable salts; and a pharmaceutically acceptable carrier or excipient.

A final aspect of the present invention features a method for treating and/or preventing cardiac disease in a mammal, comprising administering to the mammal an effective amount of a compound of formula I or II or III or derivatives thereof, or their pharmaceutically acceptable salts.

BRIEF DESCRIPTION OF THE DRAWINGS

The present invention will be more fully understood and further advantages will become apparent when reference is made to the following description of the invention and the accompanying drawings in which.

DETAILED DESCRIPTION OF THE INVENTION

Figure 1:
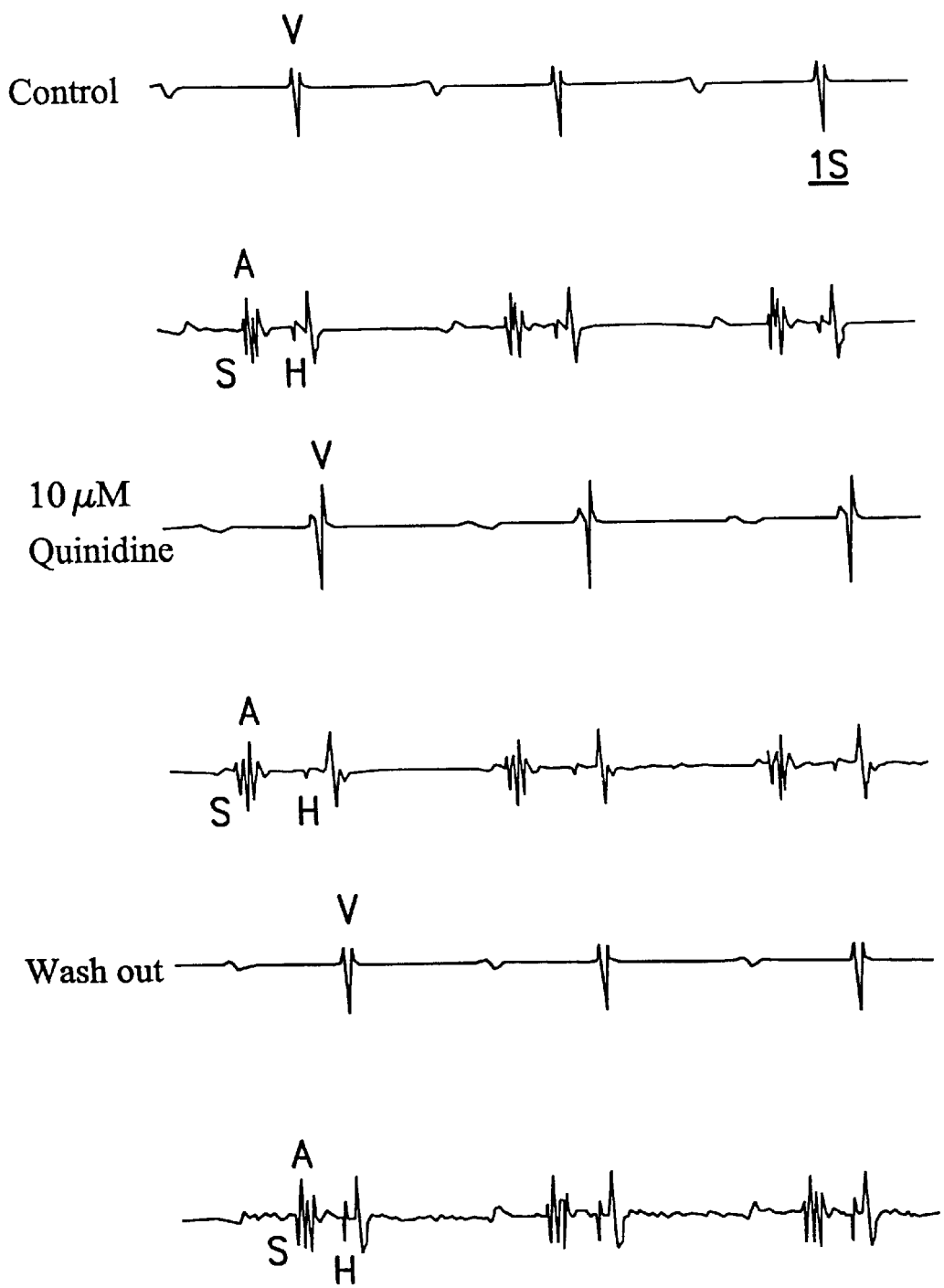
FIG. 1 is an original recording showing effects of 10 $\mu$M quinidine on AV node conduction. A: atrial-depolarization; H: His bundle depolarization; S: stimulation artifact; V: ventricular-depolarization.

Thaliporphine (hereinafter abbreviated as THP) is a natural compound of phenolic aporphine alkaloid isolated from plants of several families such as Lauraceae. Previous studies revealed that THP is a partial $Ca^{2+}$ channel agonist with strong $Na^+$ and $K^+$ channel blocking activities. Though $Na^+$ and $K^+$ channel blocking activities of THP may reduce the incidence and severity of arrhythmia during cardiac ischemia or ischemia-reperfusion, the $Ca^{2+}$-channel activation of this agent can increase $Ca^{2+}$ overload and induce cardiac arrhythmia during ischemia or ischemia-reperfusion.

In the embodiments of the present invention, the effects of THP or its derivatives on arrhythmia are evaluated using isolated hearts of guinea pigs by global ischemia-reperfusion and compare with the traditional model of using rats by ligation-reperfusion.

In another embodiment of the present invention, 0.6–0.8 $\mu$M ouabain is used for inhibiting $Na^+/K^+$ pump to increase the heart contraction and induce cardiac arrhythmia in the guinea pig, followed by administering THP or its derivatives to observe the effect on ouabain induced arrhythmia.

In an alternatively embodiment of the present invention, THP is administered intravenously to observe the survival rate, the incidence and severity of arrhythmia in vivo during cardiac ischemia or ischemia-reperfusion, and the range of myocardial necrosis during cardiac ischemia.

In addition, a comparison of THP with current antiarrhythmia drugs is made via the electrophysiological effect on rats and guinea pigs to evaluate the scavenging of the free radicals by THP or its derivatives, and to determine any change in the concentration of lactate dehydrogenase (LDH) in animal blood. The increase in LDH level can serve as an indicator of myocardial injury. Further, the effects of THP or its derivatives on the production of nitric oxide (NO) in animal blood during cardiac ischemia or ischemia-reperfusion are also evaluated in the present invention.

According to one aspect of the present invention, a pharmaceutical composition comprising THP or its derivatives, or esters or pharmaceutically acceptable salts thereof is administered orally or by injection to a patient in need. In addition, the pharmaceutical composition can also comprises a pharmaceutically acceptable carrier or excipient to be administered orally or by injection to a patient in need. The formulation of such pharmaceutical composition is well-known to those skilled in this art.

As used herein, the pharmaceutically acceptable salts include salts with inorganic acids, such as hydrochloride, hydrobromide, sulfate and phosphate; salts with organic acids, such as acetate, maleate, tartrate, methanesulfonate; and salts with amino acids, such as arginine, aspartic acid and glutamic acid. Suitable pharmaceutical forms include gosterile aqueous solutions or dispersions, sterile powders, tablets, troches, pills, capsules and the like. In addition, the active compounds may be incorporated into sustained-release preparations and formulations. The pharmaceutically acceptable carrier includes any and all solvents, disintegrating agents, binders, excipients, lubricants, absorption delaying agents and the like. And while the compound of the present invention may also be present as an ester, it is a matter of course that these esters are also included in the scope of the present invention.

Without intending to limit it in any manner, the present invention will be further illustrated by the following examples.

EXAMPLE 1

Preparation of Thaliporphine
1. Preparation of Norglaucine The stem of Phoebe formosana (Hayata) Hayata was extracted with 2% acetic acid (60° C., thrice) to obtain (+)-laurolitsine-rich extract. To 50 g of crude (+)-laurolitsine in a 500 ml reaction bottle were added 250 ml of N,N-dimethylformamide (DMF) and 40 ml of ethyl formate. The mixture was stirred at 90° C. for 60 hours, followed by re-crystallization with methanol to obtain 7.5 g of N-formyllaurolitsine. Physical data were as follows: mp: 275–277° C.; $^1$H NMR (CD$_3$OD, 400 MHz) δ 8.61, 8.44 (1H, s, N-C$\underline{H}$O), 8.45, 8.40 (1H, s, H-11), 7.21, 7.16 (1H, s, H-8), 6.61 (1H, s, H-3), 3.89 (3H, s, 10-OMe), 3.58 (3H, s, 1-OMe); EIMS (70 eV) m/z (rel. int. %) 341(90), 296(40), 283(100), 240(30), 58(70).

N-Formyllaurolitsine (10.3 g, 29.4 mmol), methanol (100 ml), potassium carbonate (12.3 g) and iodomethane (13 ml) were placed in a reaction bottle. The mixture was degased under reduced pressure for 2 minutes and the bottle was sealed. The mixture was then stirred at 60° C. for 24 hours, concentrated under reduced pressure, and partitioned between chloroform (300 ml) and water (150 ml×2). The organic phase was dried over Na$_2$CO$_3$, filtered and concentrated under reduced pressure. The residue was re-crystallized with methanol to obtain a needle form of N-formylnorglaucine (9.5 g, 87%). Physical data were as follows: mp: 151–152° C.; $^1$H NMR (CDCl$_3$, 400 MHz) δ 8.37, 8.23 (1H, s, N-C$\underline{H}$O), 8.12, 8.11 (1H, s, H-11), 6.78, 6.74 (1H, s, H-8), 6.63, 6.60 (1H, s, H-3), 4.46 (dd, J=14.4, 4.3 Hz), 4.89 (1H, dd, J=13.9, 4.2 Hz, H-6a), 3.90 (9H, s, 3×OMe), 3.65 (3H, s, 1-OMe); EIMS (70 eV) m/z (rel. int. %) [M]$^+$ 365(5), 355(100), 340(40).

N-Formylnorglaucine (2.00 g, 5.42 mmol), potassium hydroxide (2.30 g, 41.5 mmol) and ethanol (50 ml) were placed in a 100 ml reaction bottle. The mixture was heated under reflux for 3 hours (Chastanet J. et al., *Heterocycles*, 1992, 34:1565–1572), concentrated under reduced pressure, and fractionated between water (100 ml) and chloroform (300 ml×3). The organic phase was dried over Na$_2$SO$_4$, filtered and concentrated under reduced pressure to give a solid which was purified by column chromatography (silica gel, with 0.2% methanol/chloroform as the eluant) to obtain (+)-norglaucine (1.75 g, 95%). Physical data were as follows: amorphous solid; [α]$_D^{24}$+77.1° (c=0.35, CHCl$_3$); $^1$H NMR (CDCl$_{3,\ 400}$ MHz) δ 8.09 (1H, s, H-11), 6.73 (1H, s, H-8), 6.58 (1H, s, H-3), 3.90 (3H, s, 9-OMe), 3.88 (3H, s, 10-OMe), 3.86 (3H, s, 2-OMe), 3.65 (3H, s, 1-OMe), 3.81 (1H, dd, J=13.9, 4.2 Hz, H-6a); HR LC/MS m/z [M+H]$^+$ 342.1682 (Calculated for C$_{20}$H$_{24}$NO$_4$ 342.1705).

2. Preparation of (+)-Thaliporphine (THP)
Norglaucine (1.90 g, 5.2 mmol), methanol (50 ml) and 35.5% formaldehyde (6.0 ml) were successively placed in a 250 ml reaction bottle. To the mixture, NaBH$_4$ was added portionwise (total 2.0 g, 52 mmol) at room temperature while stirring. The mixture was then reacted for 6 hours, concentrated under reduced pressure, and fractionated between water (150 ml) and chloroform (150 ml×3). The organic phase was washed with brine, dried over Na$_2$SO$_4$, filtered and concentrated under reduced pressure to produce a solid which was purified by column chromatography (silica gel, with chloroform as the eluant) to obtain solid product glaucine (1.78 g, 90%). Physical data were as follows: mp: 112–114° C. (diethyl ether); [α]$_D^{24}$ +120.0° (c=0.30, MeOH); $^1$H NMR (CDCl$_3$, 400 MHz) δ 8.06 (1H, s, H-11), 6.75 (1H, s, H-8), 6.56 (1H, s, H-3), 3.91 (3H, s, 9-OMe), 3.88 (3H, s, 10-OMe), 3.86 (3H, s, 2-OMe), 3.64 (3H, s, 1-OMe), 2.54 (3H, s, N-Me).

To glaucine (3.02 g, 8.45 mmol) in a 100 ml reaction bottle, 6.0 ml of 90% sulfuric acid was added in an ice bath environment (Castedo L. et al., *Heterocycles*, 1980, 14:1135–1138). The mixture was degased under reduced pressure for 2 minutes and the bottle was sealed. After stirring in the dark at room temperature for 13 days, the reaction mixture was poured into a flask containing 100 ml of ice water while stirring. The mixture was titrated to pH 8.0 with ammonia water (25%), and then was extracted with chloroform (80 ml×3). The organic phase was dried over Na$_2$SO$_4$, filtered and concentrated under reduced pressure to give a residue (3.48 g) which was purified by column chromatography (silica gel, with 1–3% methanol/chloroform as the eluant) to obtain thaliporphine (1.82 g, 62% yield). Physical data were as follows: mp: 185–187° C. (MeOH); [α]$_D^{24}$ +66.7° (c=0.31, MeOH); $^1$H NMR (CDCl$_3$, 400 MHz) δ 8.03 (1H, s, H-11), 6.76 (1H, s, H-8), 6.52 (1H, s, H-3), 3.90 (6H, s, 2-Ome and 9-OMe), 3.88 (3H, s, 10-OMe), 2.53 (3H, s, N-Me); EIMS (70 eV) m/z (rel. int. %) [M]$^+$ 341(100), 326(34), 298(24), 267(28).

EXAMPLE 2

Preparation of (+)-N-Propylnorthaliporphine
1. Preparation of (+)-N-Propylnorglaucine
According to the method of preparing N-formyllaurolitsine described in Example 1, 30 g of crude laurolitsine was dissolved in a mixture of DMF (75 ml) and propionic anhydride (6 ml). The mixture was reacted at room temperature for 24 hours, and then re-crystallized with methanol to obtain 8.02 g of N-propionyllaurolitsine. Physical data were as follows: mp: 185–189° C.; $^1$H NMR (CD$_3$OD, 400 MHz) δ 8.06 (1H, s, H-11), 3.71 (1H, s, H-8), 6.61 (1H, s, H-3), 3.88 (3H, s, 10-OMe), 3.59 (3H, s, 1-OMe), 2.52 (2H, q, J=7.2 Hz, NCOC$\underline{H}_2$CH$_3$), 1.16 (3H, t, J=7.2 Hz, NCOCH$_2$C$\underline{H}_3$); EIMS (70 eV) m/z (rel. int. %) [M]$^+$ 369(100), 296(87), 283(85), 269(44), 240(16), 57(34).

To the mixture of N-propionyllaurolitsine (2.50 g, 6.78 mmol), methanol (25 ml) and potassium carbonate (2.60 g) was added iodomethane (3.5 ml, 56.2 mmol). Under similar reaction conditions and work up to the method in Example 1, N-propionylnorglaucine (2.21 g, 82.4%) was obtained.

Physical data were as follows: mp: 150–152° C. (MeOH); $^1$H NMR (CDCl$_3$, 400 MHz) δ 8.13 (1H, s, H-11), 6.76 (1H, s, H-8), 6.60 (1H, s, H-3), 3.89 (3H, s, 9-OMe), 3.87 (6H, s, 2-Ome or 10-OMe), 3.59 (3H, s, 1-OMe), 2.45(2H, q, J=7.2 Hz, NCOC$\underline{H}_2$CH$_3$), 1.18 (3H, t, J=7.2 Hz, NCOCH$_2$C$\underline{H}_3$); EIMS (70 eV) m/z (rel. int. %) [M]$^+$ 397(79), 324(58), 311(100), 265(16), 57(20).

To a dry reaction bottle was added anhydrous THF (15 ml) and LiAlH$_4$ (380 mg, 10 mmol) successively, and the mixture was stirred for 10 minutes. To the suspending mixture was added the solution of N-propionylnorglaucine (4.01 g, 10.1 mmol) in anhydrous THF (5 ml) dropwise. The mixture was heated under reflux for 2 hours. To the mixture in an ice bath environment was added Na$_2$SO$_4$.10H$_2$O to destroy the excess LiAlH$_4$. The mixture was then filtered through Celite pad and the residue was washed with chloroform. The combined filtrate and washings were concentrated and recrystallized with diethyl ether to obtain N-propylnorglaucine (3.36 g, 86%). Physical data were as follows: mp: 95–97° C.; $[\alpha]_D^{24}$ + 106.7° (c=0.33, MeOH) ; $^1$H NMR (CDCl$_3$, 400 MHz) δ 8.03 (1H, s, H-11), 6.75 (1H, s, H-8), 6.54 (1H, s, H-3), 3.86 (3H, s, 9-OMe), 3.83 (6H, s, 2-Ome or 10-OMe), 3.60 (3H, s, 1-OMe), 2.88 and 2.43 (2H, m, N-C$\underline{H}_2$C$_2$H$_5$), 1.50 (2H, m, N-CH$_2$C$\underline{H}_2$CH$_3$), 0.93 (3H, t, J=7.2 Hz, N-C$_2$H$_4$C$\underline{H}_3$); EIMS (70 eV) m/z (rel. int. %) [M]$^+$ 383(100), 368(82), 354(45), 352(36), 281(19).

2. Preparation of (+)-Propylnorthaliporphine

N-Propylnorglaucine (1.20 g, 10.3 mmol) was reacted with 90% sulfuric acid (3 ml) according to the method for preparing (+)-THP as described in Example 1 to obtain (+)-propylnorthaliporphine (346 mg, 30% yield). Physical data were as follows: mp: 66–70° C. (MeOH); $[\alpha]_D^{24}$ +60.20 (c=0.33, MeOH); $^1$H NMR (CDCl$_3$, 400 MHz) δ 8.00 (1H, s, H-11), 6.75 (1H, s, H-8), 6.51 (1H, s, H-3), 3.90 (6H, s, 2-Ome or 9-OMe), 3.89 (3H, s, 10-OMe), 2.60 (1H, m) and 2.43 (1H, m) (N-C$\underline{H}_2$CH$_3$), 1.57 (2H, m, N-CH$_2$C$\underline{H}_2$CH$_3$), 0.95 (3H, t, J=7.2 Hz, N-C$_2$H$_4$C$\underline{H}_3$); EIMS (70 eV) m/z (rel. int. %) [M]$^+$ 369(100), 354(22), 340(36), 298(20).

EXAMPLE 3

Electrophysiological Effect of THP on Rats and Guinea Pigs

Profile of Electrogram

Figure 2:
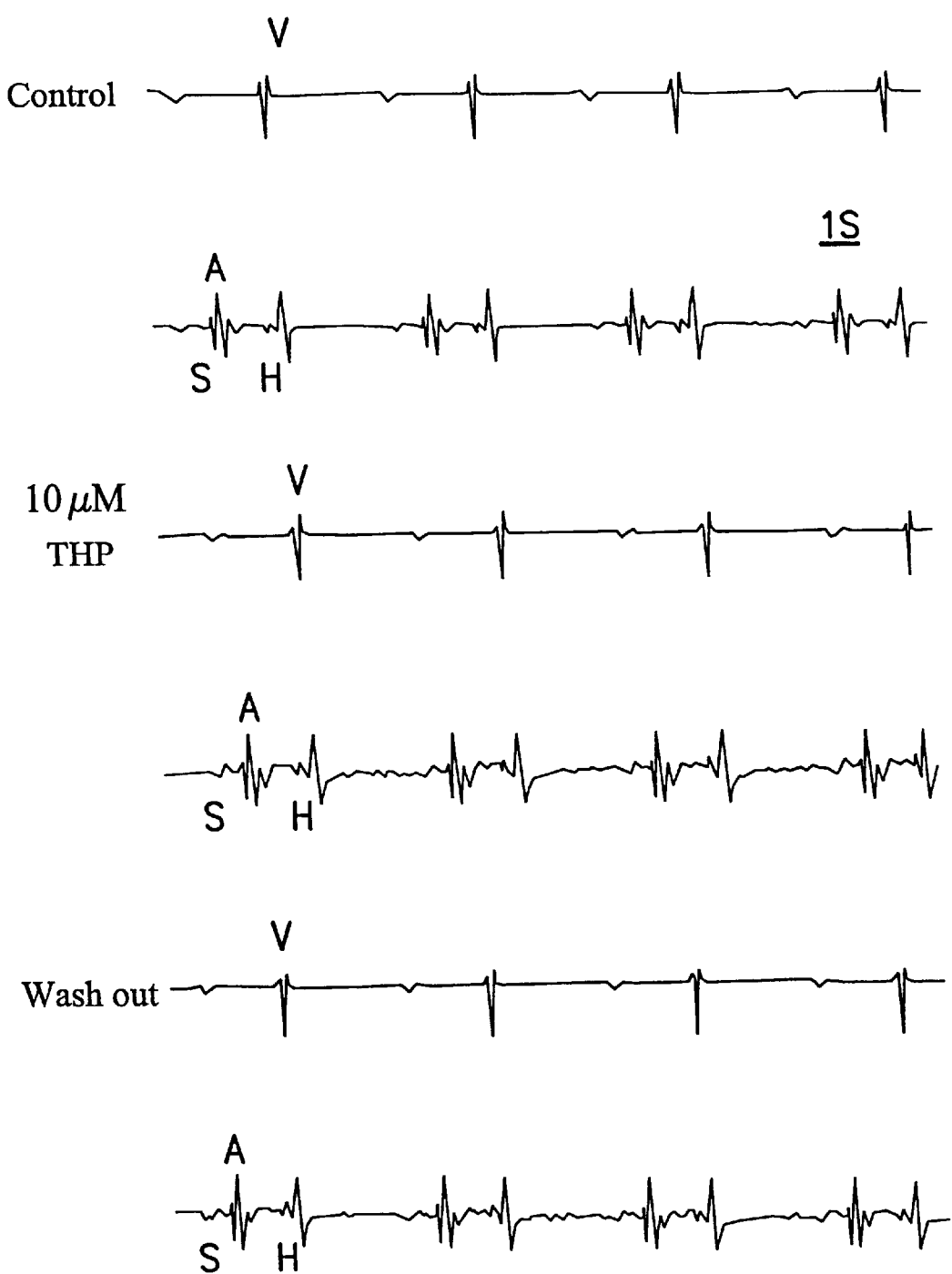
FIG. 2 is an original recording showing effects of 10 $\mu$M thaliporphine on AV node conduction. A: atrial-depolarization; H: His bundle depolarization; S: stimulation artifact; V: ventricular-depolarization.

The investigation conforms to the Guide for the Care and Use of Laboratory Animals published by the US National Institutes of Health (NIH publication No. 85-23, revised 1996). Adult rats and guinea pigs were killed after hepariniation and anesthetization with urethane (1.25 g/kg i.p.). After isolating the heart, the aorta was perfused with 10 μM quinidine and THP, respectively, by Langendorff perfusion. A pair of bipolar electrodes connected with silver wire were placed on the tip of the Triangle of Koch to record the His bundle electrogram. In addition, another pair of bipolar electrodes connected with silver wire were placed on the surface of the right ventricle to record T wave. The right atrium near the superior vena cava was paced at a constant rate with a pacing cycle length of 300 ms. The QT interval, conduction time through the sinoatrial (SA interval), the atrioventricular node (AH interval) and His-purkinje system (HV interval) were recorded, respectively, using electrocardiograph. Similarly, the recovery curve of His-purkinje system (i.e. the relationship of H$_2$V$_2$ and V$_1$H$_2$), atrial and ventricular refractory period and AV node refractory period were also recorded in the same manner. The results are shown in FIGS. 1 and 2.

EXAMPLE 4

Antioxidant and Free Radical Scavenging Activities of THP or its Derivatives

Figure 3:
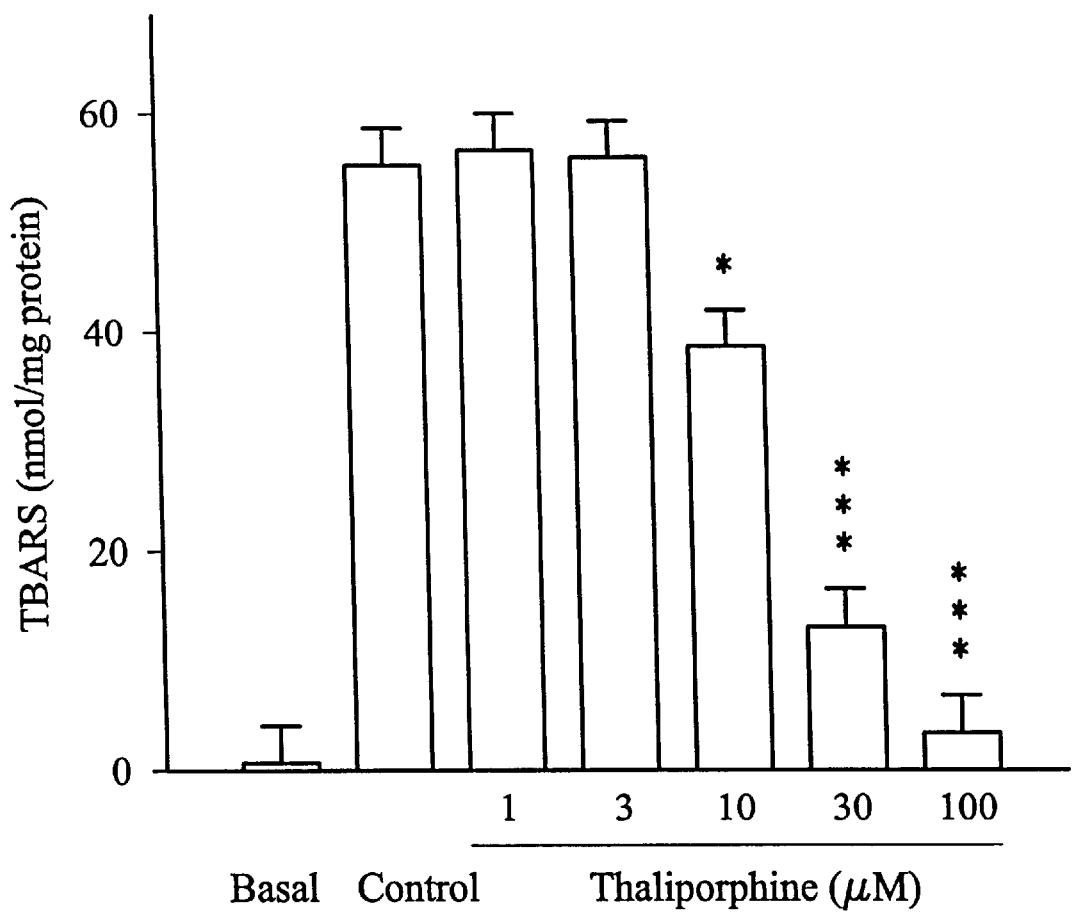
FIG. 3 is a diagram the inhibitory effects of thaliporphine on lipid peroxidation of human LDL induced by copper. Data are presented as mean±SE (n=4). *p<0.05, p<0.01, *p<0.001, as compared with the control.

Human low density lipoprotein (LDL, 100 μg/ml) was preincubated with DMSO (0.1%, basal and control) or various concentrations of THP at 37° C. for 10 minutes, and then CuSO$_4$ was added, except for basal, and incubated for another 12 hours to determine the impact of THP on lipid peroxidation. The result is shown in FIG. 3.

Figure 4:
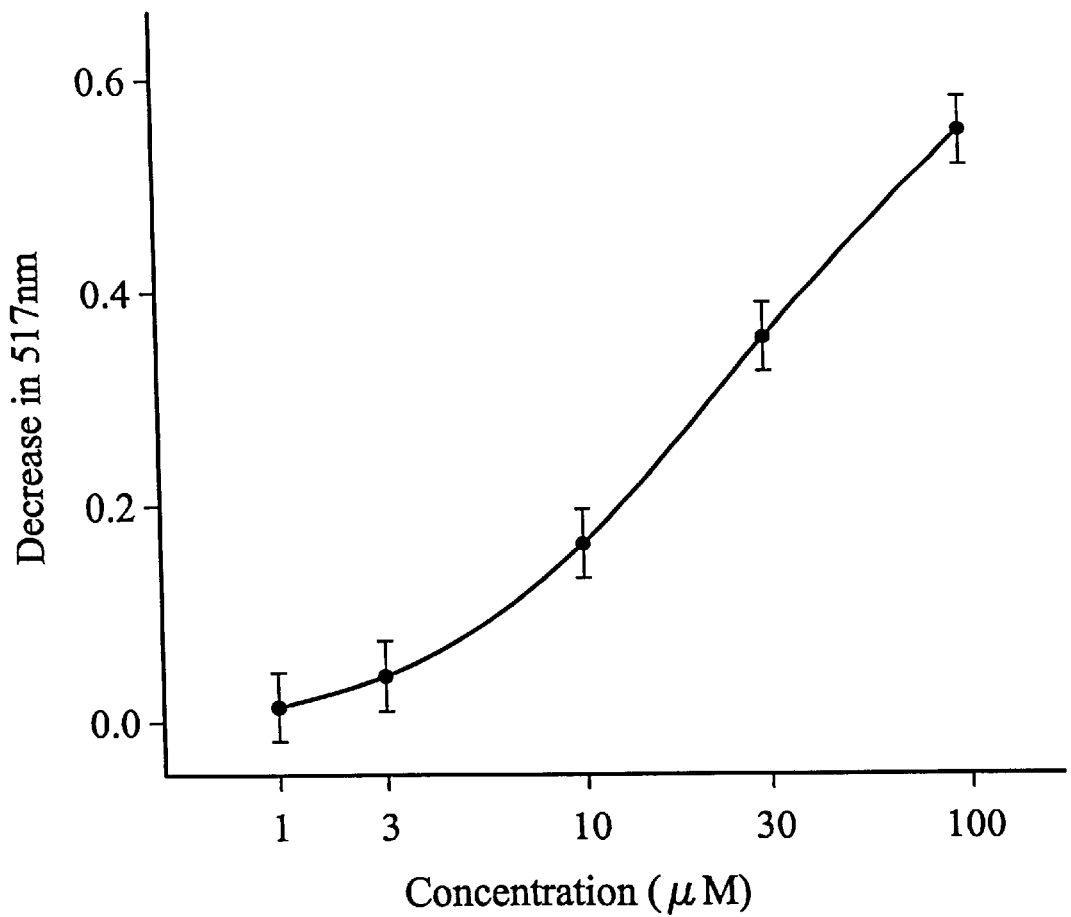
FIG. 4 is a dose-response curve of thaliporphine in scavenging DPPH radicals. Data are presented as mean±SE (n=4).

After incubation of various concentrations of THP with 1,1-diphenyl-2-picrylhydrazyl (DPPH, 100 μM) at room temperature (25° C.) for 30 minutes, decrease in the absorbance for DPPH at 517 nm was measured to determine the dose-response curve of THP in scavenging DPPH radicals. The result is shown in FIG. 4.

EXAMPLE 5

Antiarrhythmia Effect of THP or its Derivatives

1. Rat Arrhythmia Induced by Ligation-Reperfusion

Figure 5A:
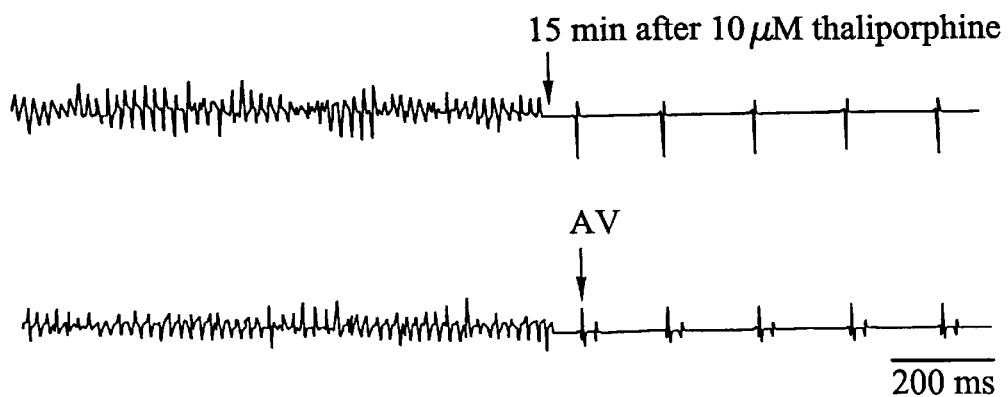
FIG. 5 is a diagram showing (a) conversion of polymorphic ventricular tachyrhythmia induced by ischemia-reperfusion to normal sinus rhythm by 10 $\mu$M thaliporphine, indicating atrial (A) and ventricular (V) depolarization; (b) antiarrhythmic efficiency of thaliporphine.
Figure 5B:
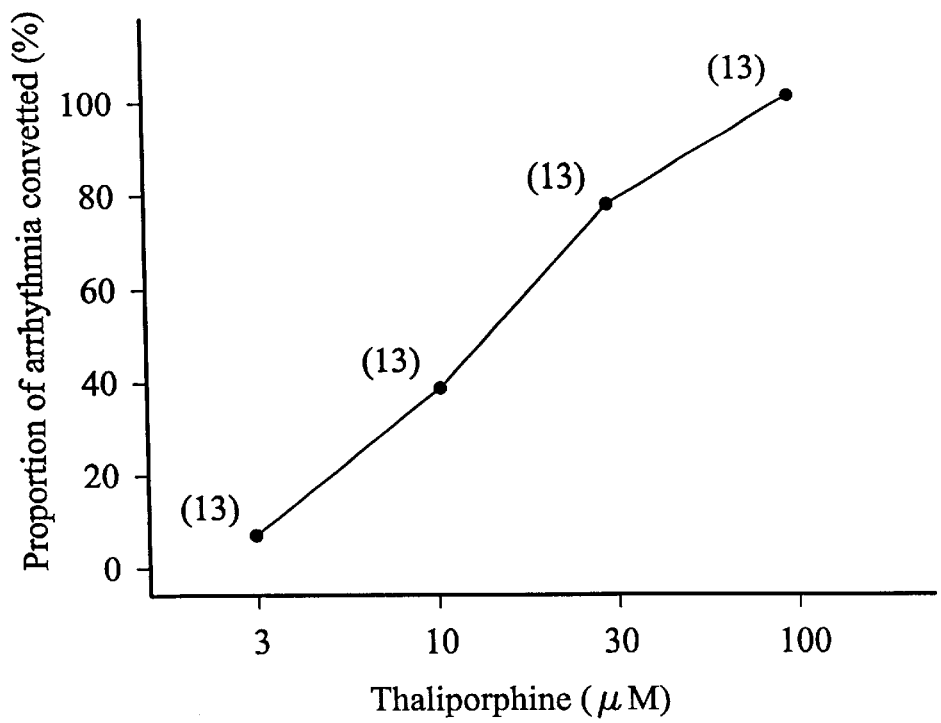

The isolated rat hearts were ligated by a temporary tightening of the silk ligature around the left main coronary artery to induce myocardial ischemia. Reperfusion was achieved by releasing the tension applying to the ligature to induce arrhythmia. 10 μM THP was then administered and the atrial and ventricular electrograms were recorded. The result is shown in FIG. 5.

2. Guinea Pig Arrhythmia Induced by Global Ischemia-Reperfusion

The isolated guinea pig hearts were ligated by global ischemia. Reperfusion was achieved by releasing the tension appliyed to the ligature. Various concentrations of THP were then administered and the ventricular fibrillarion (VF) was recorded. The result is shown in Table 1.

TABLE 1

| Effects of THP on reperfusion-induced ventricular fibrillation in isolated guinea pig hearts subjected to global ischemia | | | |
| --- | --- | --- | --- |
| Treatment | n | VF | % VF |
| DMSO (0.1%) | 8 | 8 | 100 |
| 3 μM | 8 | 2 | 25* |
| 10 μM | 6 | 0 | 0* |

Significantly different (*p < 0.05) from corresponding vehicle value. n represents number of hearts studied.

3. Guinea Pig Arrhythmia Induced by Ouabain

Figure 6A:
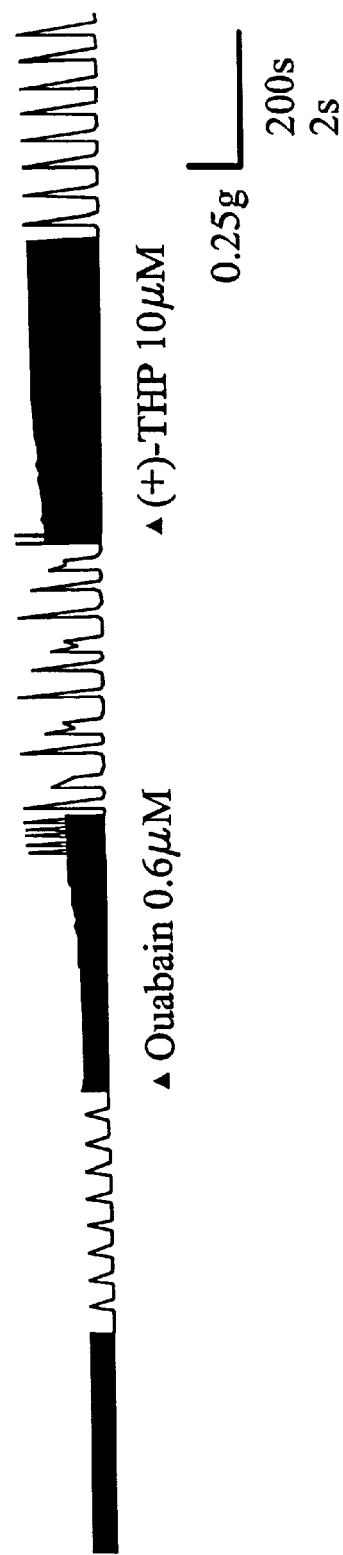
FIGS. 6–7 are diagrams showing ouabain-induced cardiac arrhythmia in electrically driven guinea pig right ventricular strips.
Figure 6B:
Figure 7A:
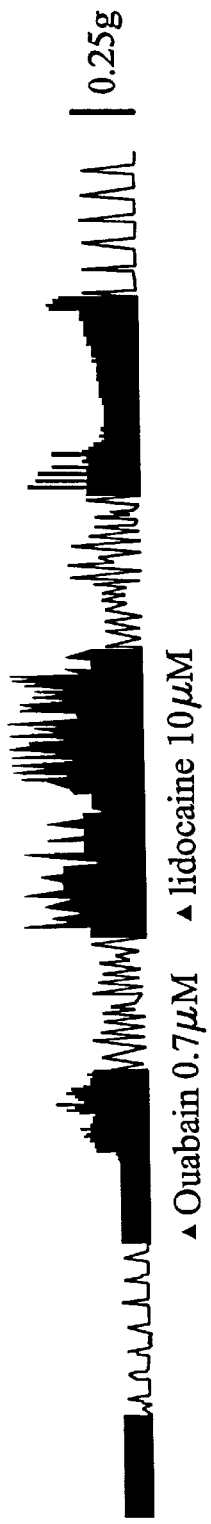
Figure 7B:
Figure 7C:
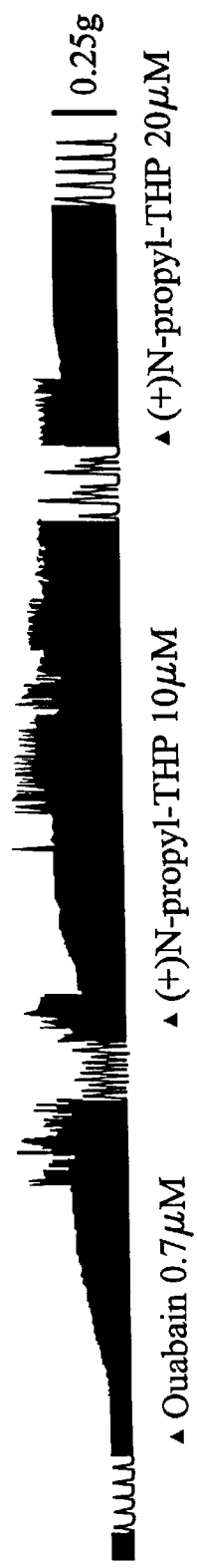

After administering 0.6–0.8 μM ouabain to guinea pig ventricles, an increased contraction was observed. The arrhythmia was then induced 5–10 minutes after. 10–20 μM THP or its derivatives were administered to reverse the ouabain-induced arrhythmia. The results are shown in FIGS. 6–7.

4. Clinical Uses of THP in Rats

Myocardial ischemia was performed by a temporary tightening of the silk ligature around the left main coronary artery. Reperfusion was achieved by releasing the tension applied to the ligature (operated groups). Sham operated animals underwent all surgical procedures, apart from the fact that the silk, passing around the left coronary artery, was not tied (sham groups). Animals were infused with a bolus of THP (3.5×10$^{-7}$, 3.5×10$^{-6}$, 3.5×10$^{-5}$ g/kg), L-NAME (N$^\omega$-nitro-L-arginine methyl ester; 1×10$^{-3}$ g/kg) or vehicle (dimethyl sulfoxide/NaCl 0.9%, 1:10$^3$; v/v) from a jugular vein 15 minutes before coronary occlusion. The coronary artery was occluded for 30 minutes or 5 minutes followed by 30 minutes reperfusion and with the animals then divided randomly in the following groups: (1) sham+vehicle; (2) sham+THP (3.5×10$^{-5}$ g/kg); (3) operated+vehicle; (4) operated+THP (3.5×10$^{-7}$ g/kg); (5) operated+THP (3.5×

$10^{-6}$ g/kg); (6) operated+THP ($3.5 \times 10^{-5}$ g/kg); (7) operated+L-NAME ($1 \times 10^{-3}$ g/kg)+THP ($3.5 \times 10^{-5}$ g/kg). Before and during the ischemia or reperfusion period, heart rate (HR), blood pressure (BP) and ECG changes were recorded. Ventricular ectopic activity was evaluated according to the diagnostic criteria advocated in the Lambeth Convention. The incidence and duration of ventricular tachyarrhythmias, including ventricular tachycardia (VT) and ventricular fibrillation (VF), in surviving animals was determined. The Mann-Whitney rank-sum test was used to analyze the differences in the duration of VT and VP between vehicle and drug treated groups. The BP and HR changes between vehicle and drug treated rats in the arrhythmia study were analyzed by ANOVA (analysis of variance) followed by Bonferroni's test. The difference in the percentage incidence of VT, VF and mortality rate was analyzed with a Chi-square test. The results are shown in Tables 2–3.

TABLE 2

Effect of THP on ischemia-induced arrhythmias in the in vivo anesthetized rat

| THP (g/kg) | VT Incidence (%) | VT Duration (s) | VF Incidence (%) | VF Duration (s) | Mortality (%) |
|---|---|---|---|---|---|
| 0 (vehicle) | 100 | 36.8 ± 8.8 | 57 | 32.1 ± 8.9 | 29 |
| $3.5 \times 10^{-7}$ | 60 | 16.1 ± 7.4 | 20 | 6.7 ± 4.9 | 0 |
| $3.5 \times 10^{-6}$ | 50* | 5.7 ± 3.3* | 10 | 0.5 ± 0.5* | 0 |
| $3.5 \times 10^{-5}$ | 10* | 0.3 ± 0.3* | 0* | 0.0 ± 0.0* | 0 |
| THP $3.5 \times 10^{-5}$ + L-NAME $1 \times 10^{-3}$ | 65 | 23.3 ± 10.0 | 64 | 32.9 ± 13.1 | 27 |

Values for duration of VT, VF are shown as mean ± SE of 10–14 rats.
*Statistical difference at the level of p < 0.05. Vehicle is 0.01% DMSO in normal saline. n = 10–12.

TABLE 3

Effect of THP on reperfusion-induced arrhythmias in the in vivo anesthetized rat

| THP (g/kg) | VT Incidence (%) | VT Duration (s) | VF Incidence (%) | VF Duration (s) | Mortality (%) |
|---|---|---|---|---|---|
| 0 (vehicle) | 100 | 17.4 ± 5.6 | 88 | 92.4 ± 20.5 | 75 |
| $3.5 \times 10^{-7}$ | 86 | 28.6 ± 10.4 | 86 | 75.5 ± 15.6 | 43 |
| $3.5 \times 10^{-6}$ | 57 | 14.6 ± 9.1 | 29* | 9.2 ± 8.3* | 0* |
| $3.5 \times 10^{-5}$ | 71 | 7.6 ± 3.2 | 14* | 1.2 ± 1.2* | 0* |
| THP $3.5 \times 10^{-5}$ + L-NAME $1 \times 10^{-3}$ | 89 | 16.5 ± 8.5 | 44 | 42.8 ± 20.2 | 33 |

Values for duration of VT, VF are shown as mean ± SE of 7–16 rats.
*Statistical difference at the level of p < 0.05. Vehicle is 0.01% DMSO in normal saline. n = 7.

Infarct size was determined by the triphenyl tetrazolium chloride-Evan's blue staining technique. The rat was sacrificed after its left descending coronary artery had been occluded for 4 hours. The weight of infarct tissue was expressed as a percentage of total ventricular weight or occluded zone. The difference in infarct size was statistically analyzed using unpaired Student's t-test. The results are shown in Table 4.

TABLE 4

Area at risk and infarct size in vehicle and THP-treated rats subjected to 4 hours coronary ligation

| Treatment (g/kg) | n | Area at risk (% of ventricle) | Necrotic (% of ventricle) | Necrotic (% of Area at risk) |
|---|---|---|---|---|
| 0 (vehicle) | 10 | 45.2 ± 1.0 | 19.8 ± 2.2 | 43.9 ± 5.1 |
| $3.5 \times 10^{-7}$ | 9 | 47.0 ± 0.6 | 17.9 ± 2.3 | 38.1 ± 5.0 |
| $3.5 \times 10^{-6}$ | 8 | 46.5 ± 0.9 | 13.4 ± 1.2* | 29.0 ± 2.5* |
| $3.5 \times 10^{-5}$ | 11 | 46.9 ± 0.5 | 5.0 ± 0.9*** | 10.7 ± 1.8*** |
| L-NAME $1 \times 10^{-3}$ | 9 | 47.5 ± 0.2 | 21.4 ± 3.5 | 45.1 ± 7.2 |
| THP $3.5 \times 10^{-5}$ + L-NAME $1 \times 10^{-3}$ | 8 | 47.0 ± 0.4 | 21.8 ± 4.0 | 46.5 ± 6.6 |

Values are presented as mean ± SE. n, number of animals.
Vehicle is 0.01% DMSO in normal saline. *p < 0.05, p < 0.01, *p < 0.001, as compared with vehicle.

Cellular damage was evaluated by measuring the plasma LDH. Arterial blood samples were drawn from the carotid catheter at the end of ischemia or ischemia-reperfusion, collected in heparinized tubes. The blood was kept at 4° C. until it was centrifuged at 2000×g for 15 minutes. The plasma was recovered and aliquots were used for determination of LDH activity with a commercial kit from Sigma. The deproteinized plasma samples were frozen and kept until analysis. NO was measured by the No/ozone chemiluminescence technique described in Yanu F. et al., (1997) Clin. Chem. 43:657–662. The difference in plasma NO and LDH were analyzed statistically using unpaired Student's t-test. The results are shown in Tables 5–6.

TABLE 5

Effects of THP on LDH (U/L) release

| Treatment (g/kg) | Non-ischemic | Ischemic | Reperfused |
|---|---|---|---|
| Sham-operated | | | |
| Vehicle | 123.6 ± 20.6 | | |
| THP $3.5 \times 10^{-5}$ | 92.6 ± 7.5 | | |
| Operated | | | |
| Vehicle | | 500.5 ± 81.4*** | 273.7 ± 29.2*** |
| THP $3.5 \times 10^{-7}$ | | 349.5 ± 55.0 | 202.2 ± 30.4 |
| THP $3.5 \times 10^{-6}$ | | 171.7 ± 56.9*** | 219.6 ± 31.0 |
| THP $3.5 \times 10^{-5}$ | | 132.2 ± 33.2*** | 143.8 ± 11.7*** |

Values are presented as mean ± SE (n = 6). Vehicle is 0.01% DMSO in normal saline. *p < 0.05, p < 0.01, *p < 0.001, as compared with vehicle.

TABLE 6

Effects of THP on NO (μmol/L) release

| Treatment (g/kg) | Non-ischemic | Ischemic | Reperfused |
|---|---|---|---|
| Sham-operated | | | |
| Vehicle | 9.6 ± 2.3 | | |
| THP $3.5 \times 10^{-5}$ | 7.6 ± 0.9 | | |
| Operated | | | |
| Vehicle | | 8.3 ± 0.6 | 8.6 ± 1.6 |
| THP $3.5 \times 10^{-7}$ | | 6.6 ± 0.6 | 8.0 ± 1.7 |

TABLE 6-continued

Effects of THP on NO (μmol/L) release

| Treatment (g/kg) | Non-ischemic | Ischemic | Reperfused |
|---|---|---|---|
| THP $3.5 \times 10^{-6}$ | | $19.4 \pm 4.7$* | $28.4 \pm 4.3$*** |
| THP $3.5 \times 10^{-5}$ | | $19.1 \pm 5.5$* | $30.4 \pm 1.9$*** |

Values are presented as mean ± SE (n = 6). Vehicle is 0.01% DMSO in normal saline. *p < 0.05, p < 0.01, *p < 0.001, as compared with vehicle.

The SA, AH, HV intervals and T wave are prolonged in the quinidine-treated heart (FIG. 1). As compared with quinidine, the S-A interval remains unaffected and the HV interval is prolonged slightly by THP, indicating that quinidine has poor selectivity. In addition, 3, 10 and 30 μM THP can prolong the atrial effective refractory period (AERP) from 60 ms to 90, 100 and 120 ms, respectively; the ventricular effective refractory period (VERP) from 160 ms to 160, 170 and 190 ms, respectively; and the AV node effective refractory period (AVNERP) from 170 ms to 170, 200 and 240 ms, respectively. When compared with THP in the same manner, 3, 10 and 30 μM quinidine can prolong the AERP from 40 ms to 60, 80 and 130 ms; the VERP from 180 ms to 170, 180 and 190 ms; and the AVNERP from 130 ms to 150, 200 and 245 ms, respectively. Further, 3, 10 and 30 μM THP can change the wenckbach cycle length (WCL) from 200 ms to 210, 230 and 280 ms, respectively; whereas 3, 10 and 30 μM quinidine can change the WCL from 150 ms to 170, 210 and 300 ms, respectively. Both THP and quinidine prolong AERP, VERP and AVNERP, however, only quinidine inhibits conduction in AV node (prolonged AH interval). In contrast, even when the THP concentration raised to 10 μM, the conduction in AV node is not inhibited.

Moreover, 3–10 μM THP prolongs the action potential duration in the atria or ventricles of both rats and guinea pigs (data not shown). Furthermore, THP can markedly inhibit the transient outward potassium current ($I_{to}$) in rats and the delayed outward potassium current ($I_K$) in guinea pigs. Furthermore, it is found that THP can inhibit the inward sodium current, but enhance the inward calcium current (Su M J, et al., *Eur. J. Pharmacol.*, 1994, 254:141–150). Therefore, THP possesses the activities of prolonging action potential, enhancing cardiac contraction and decreasing heart rate.

The impact of THP on lipid peroxidation is further assessed by evaluating its effect on the formation of TBARS (thiobarbituric acid-reactive substance) from LDL. Exposure of LDL to $CUSO_4$ within 12 hours results in the peroxidation of LDL, as indicated by the increased content of TBARS (FIG. 3). Addition of THP suppresses the formation of $CuSO_4$-induced TBARS in a concentration-dependent manner ($IC_{50}$, 15.7 μmol/L). In addition to the antioxidation of LDL, THP can scavenge superoxide anion generated by the xanthine/xanthine oxidase system in a concentration-dependent manner with $EC_{50}$ of 12.6 μM.

In the 1,1-diphenyl-2-picrylhydrazyl (DPPH) assay system, the free radical scavenging activity of THP is expressed as $IC_{0.200}$. The decrease in optical absorbance at 517 nm after addition of THP is monitored following the trapping of the unpaired electron of DPPH. Referring to FIG. 4, THP scavenges DPPH in a concentration-dependent manner with $IC_{0.200}$ of 12.4 μmol/L.

3–30 μM THP can be effective in reversing the cardiac arrhythmia induced by the isolated rat heart subjected to 30 minutes ligation followed by reperfusion with $IC_{50}$ of 15.7 μmol/L (FIG. 5). Similarly, 10 μM THP can be effective in inhibiting the cardiac arrhythmia induced in the isolated guinea pig heart subjected to global ischemia followed by reperfusion (Table 1). The structure of coronary arteries between rat and guinea pig are not alike, THP, however, can be effective in inhibiting the arrhythmia induced in the isolated heart subjected to ischemia-reperfusion in both animals.

Referring to FIGS. 6–7, after administering 0.6–0.8 μM ouabain to guinea pig ventricles, an increased contraction is observed. The arrhythmia is then induced 5–10 minutes after. The administration of 10–20 μM THP or its derivatives can be effective in reversing the arrhythmia, however, quinidine at this concentration does not reveal the efficacy (data not shown).

Figure 8:
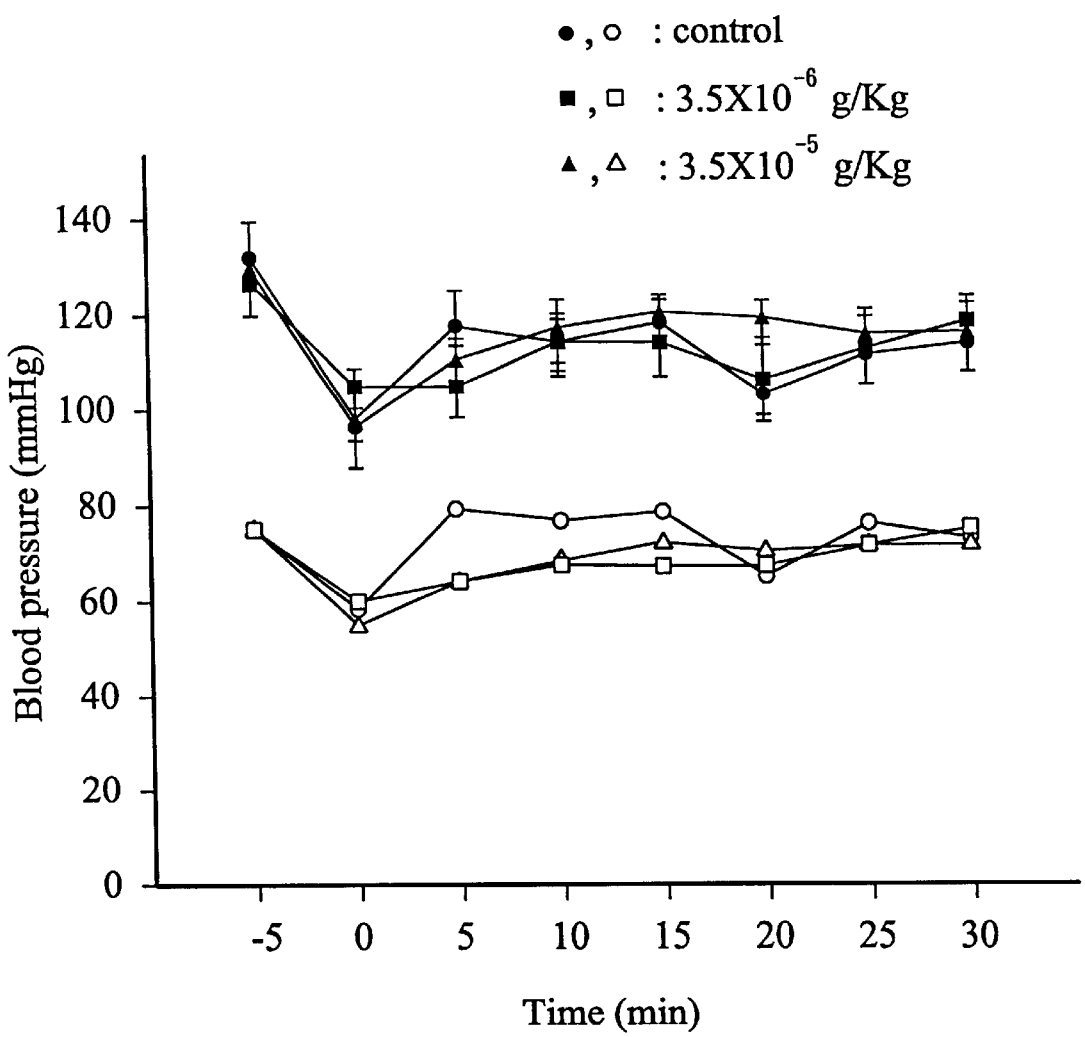
FIG. 8 is a diagram showing systolic and diastolic blood pressure in control and thaliporphine treated rats subjected to 30 minutes of coronary ligation. The differences between the control and the two concentrations of thaliporphine are statistically insignificant (ANOVA).
Figure 9:
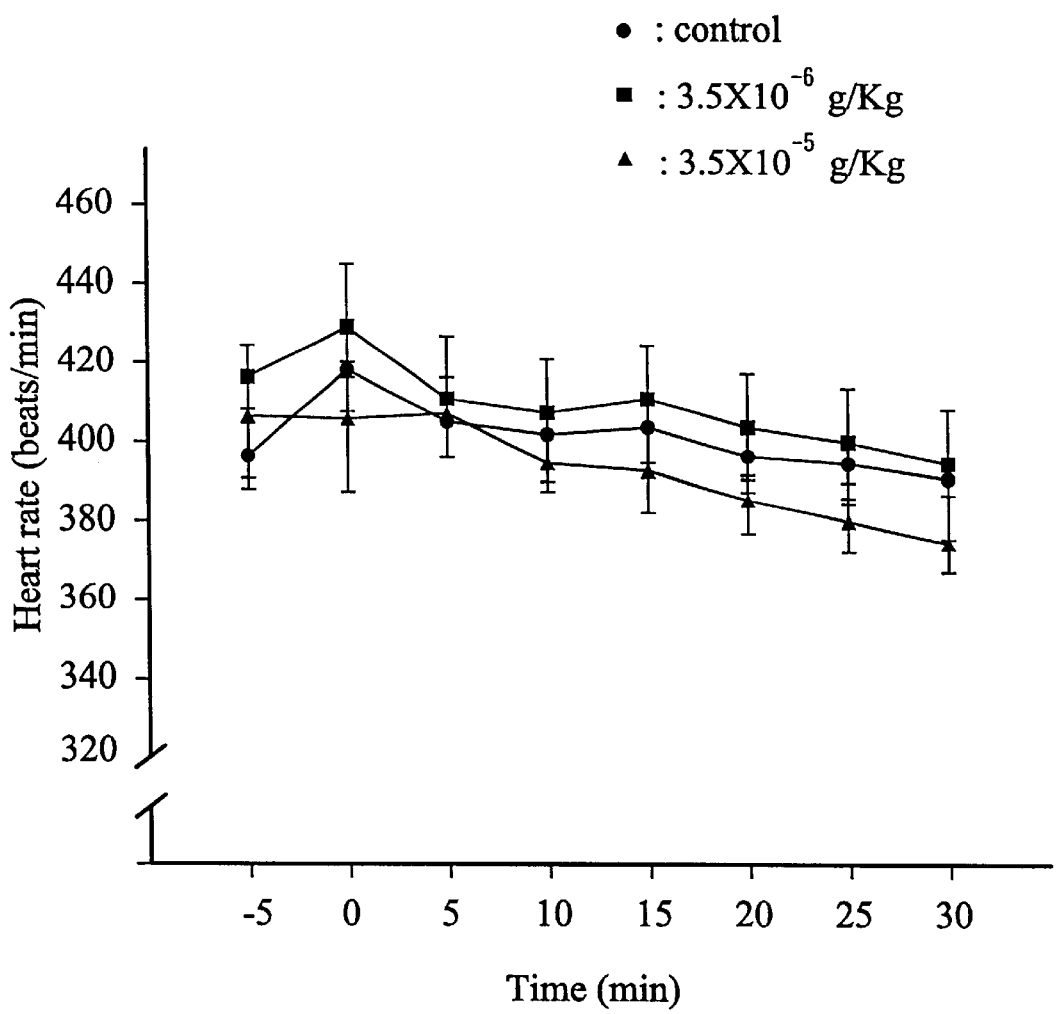
FIG. 9 is a diagram showing heart rate in control and thaliporphine treated rats subjected to 30 minutes coronary ligation. The differences between the control and the two concentrations of thaliporphine are statistically insignificant (ANOVA).

Intravenous administration of THP does not modify the diastolic, systolic blood pressure and heart rate (HR) in rats subjected to myocardial ischemia (FIGS. 8–9). No significant difference can be seen among vehicle and drug groups ($3.5 \times 10^{-6}$ or $3.5 \times 10^{-5}$ g/kg, THP).

In ischemic condition, severe ventricular arrhythmias in the vehicle group begins after 6–7 minutes of coronary artery occlusion, peaks after 8–12 minutes, and normally subsides after approximately 15 minutes from initiation. The duration of VF is calculated to be 32.1±8.9 seconds, and the duration of VT is 36.8±8.8 seconds. Among 14 rats in the vehicle group, 57% of them exhibit VF whereas 100% exhibit VT. Administration of THP at $3.5 \times 10^{-5}$ g/kg results in a decrease of the incidence of VT and VF to 10% and 0%, respectively (p<0.05). The duration of VT and VF is markedly reduced to 0.3±0.3 seconds and 0.0±0.0 seconds (p<0.05). A particular important finding is the very effective reduction of mortality even at very low dose of THP $3.5 \times 10^{-7}$ g/kg. Moreover, in the L-NAME+THP group the incidence and duration of VT or VF and mortality is indistinguishable from that measured in the control group (operated-vehicle), indicating that L-NAME ($1 \times 10^{-3}$ g/kg) completely abolishes the antiarrythmic activities and mortality reduction efficacy of THP (Table 2).

The severity of reperfusion induced-arrhythmias is critically dependent upon the duration of the preceding period of ischemia. Thus, the protocol of a 5 minutes period of ischemia followed by a 30 minutes period of reperfusion is selected for producing the highest incidence of rhythm disturbance. Table 3 shows that in the vehicle group, about 88% of animals exhibit VF in the reperfusion period and 75% of them are dead, mainly from VF. In contrast, animals pretreated with THP ($3.5 \times 10^{-6}$ and $3.5 \times 10^{-5}$ g/kg), experienced a drastic reduction in the incidence of VF from 88% to 29% and 13% (p<0.05) and the duration of VF from 92.4±20.5 seconds to 9.2±8.3 and 1.2±1.2 seconds (p<0.05). The mortality rate also decreases from 75% to 0% by $3.5 \times 10^{-6}$ g/kg THP (p<0.05). However, L-NAME co-administration only partially antagonizes the antiarrhythmic activity and mortality prevention effect of thaliporphine ($3.5 \times 10^{-5}$ g/kg).

The difference in ischemic area and infarct size shown by staining technique after 4 hours of ischemia is evaluated. The area at risk shows no significant differences between each of the experimental groups (Table 4), indicating that a similar amount of tissue was jeopardized by the occlusion of the left coronary artery in each group. In the vehicle group, the necrotic area expresses either as a percentage of the area at risk (45.2±1.0%) or as a percentage of the total ventricle (19.8±2.2%), indicating the amount of cardiac tissue at risk becomes necrotic. Administration of THP reduces myocardial necrosis extension in a dose dependent manner. This reduction is observed either in the necrotic area/area at risk (38.1±5.0%, 29.0±2.5% and 10.7±1.8%/with $3.5\times10^{-7}$, $10^{-6}$, $10^{-5}$ g/kg of THP, respectively) or in the necrotic area/total ventricle (17.9±2.3%, 13.4±1.2% and 5.0±0.9% with $3.5\times10^{-7}$, $10^{-6}$, $10^{-5}$ g/kg of THP, respectively). However, in the L-NAME+THP group, the infarct size did not differ from that observed in the control group (operated-vehicle), indicating that L-NAME (1 mg/kg) completely abrogates the infarct-sparing effect of THP ($3.5\times10^{-5}$ g/kg).

The biochemical indicator of cellular damage (LDH release) is determined in ischemia and the ischemia-reperfusion period. Low LDH activity can be seen in the control group (123.6±20.6 U/L) before occlusion. After the occlusion or occlusion-reperfusion, a large increase of the enzyme is found in the plasma of rats given operated-vehicle (500.5±81.4 U/L and 273.7±29.2 U/L, respectively). However, administration of THP attenuates LDH release with a dose-dependent manner during ischemia or ischemia-reperfusion (Table 5).

Nitric oxide (NO) release is measured by the presence of nitrite ($NO_2^-$) and nitrate ($NO_3^-$) in the plasma from an animal with 30 minutes ischemia or 5 minutes followed by 30 minutes reperfusion. In sham animals, NO is measured to be 9.6±2.3 and 7.6±0.9 μmol/L without and with THP pretreatment, respectively. In the operated animals, THP exerts a dramatically increase of plasma NO; at a dose of $3.5\times10^{-6}$ g/kg, there are 2- and 3.5-fold increases compared to that of the untreated (vehicle) ischemic or ischemic-reperfused animals, respectively (Table 6).

In conclusion, the present invention demonstrates that THP and the related derivatives thereof, not only suppress the severity of ischemia- or reperfusion-induced ventricular arrhythmias, but also reduce infarct size after prolonged coronary occlusion. THP and its derivatives also simultaneously increase the NO and decrease the LDH levels in blood from rats submitted to regional ischemia or reperfusion. As noted above, many traditional antiarrhythmic drugs appear to have the potential for causing side effects as well as a lower effectiveness on reperfusion-induced arrhythmia. The multifactorial beneficial effects of THP and its derivatives of the present invention afford an opportunity to be used as an effective antiarrhythmic and cardioprotective agent.

While the invention has been particularly shown and described with reference to the preferred embodiment(s) thereof, it will be understood by those skilled in the art that various changes in form and details may be made without departing from the spirit and scope of the invention.

What is claimed is:

1. A compound of formula III or ester, or a pharmaceutically acceptable salt thereof

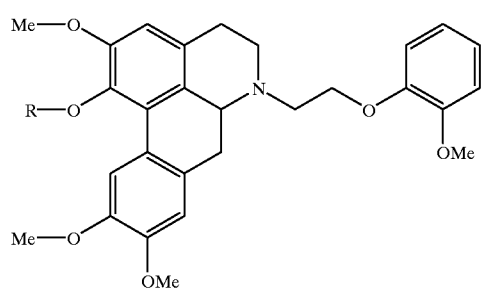

wherein R is hydrogen, acetyl, propionyl, butyryl or tert-butoxycarbonyl.

2. A pharmaceutical composition for the treatment and/or prophylaxis of a cardiac disease in a mammal, comprising:

(i) an effective amount of a compound of formula III or ester, or a pharmaceutically acceptable salt thereof:

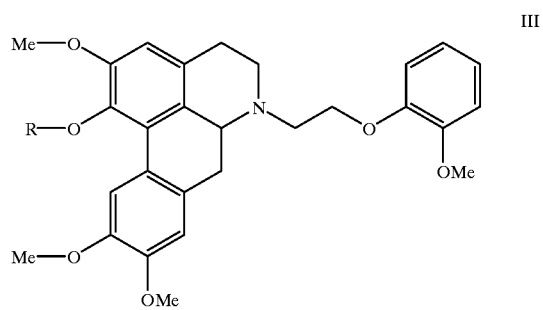

wherein R is hydrogen, acetyl, propionyl, butyryl or tert-butoxycarbonyl; and (ii) a pharmaceutically acceptable carrier or excipient.

3. The pharmaceutical composition as claimed in claim 2, wherein cardiac disease is selected from the group consisting of cardiac arrhythmia, myocardial ischemia, myocardial infarction, sudden death caused by cardiac arrhythmia, and sudden death caused by acute myocardial infarction.

4. A method for treating and/or preventing a cardiac disease selected from the group consisting of cardiac arrhythmia, myocardial ischemia, myocardial infarction, sudden death caused by cardiac arrhythmia, and sudden death caused by acute myocardial infarction in a mammal, comprising administering to the mammal in need thereof an effective amount of a compound of formula III:

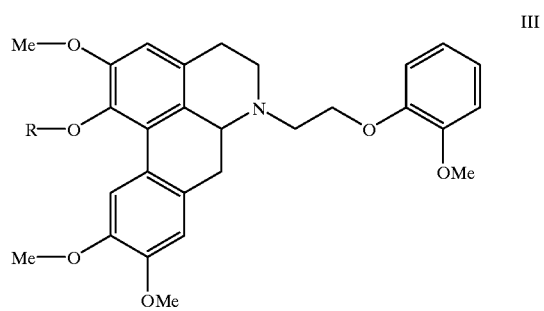

wherein R is hydrogen, acetyl, propionyl, butyryl or tert-butoxycarbonyl.

5. The method as claimed in claim 4, wherein cardiac disease is selected from the group consisting of cardiac arrhythmia, myocardial ischemia, myocardial infarction, sudden death caused by cardiac arrhythmia, and sudden death caused by.

* * * * *